United States Patent [19]

Bonte et al.

[11] Patent Number: 5,624,673
[45] Date of Patent: Apr. 29, 1997

[54] COSMETIC OR PHARMACEUTICAL COMPOSITION CONTAINING A PRUNELLA EXTRACT

[75] Inventors: Frédéric Bonte; Alain Meybeck, both of Courbevoie; Marc Dumas, Colombes, all of France

[73] Assignee: LVMH Recherche, Colombes Cedex, France

[21] Appl. No.: 150,183

[22] PCT Filed: Jun. 4, 1992

[86] PCT No.: PCT/FR92/00494

§ 371 Date: Dec. 6, 1993

§ 102(e) Date: Dec. 6, 1993

[87] PCT Pub. No.: WO92/21322

PCT Pub. Date: Dec. 10, 1992

[51] Int. Cl.$^6$ .................... A61K 35/78; A61K 47/00
[52] U.S. Cl. .................... 424/195.1; 424/423; 424/450; 514/783; 514/844; 514/845; 514/846; 514/847; 514/859; 514/860; 514/861; 514/863; 514/886; 514/887
[58] Field of Search ............... 424/195.1, 423, 424/450; 514/844, 845, 846, 847, 859, 860, 861, 863, 886, 887

[56] References Cited

U.S. PATENT DOCUMENTS

| | | | |
|---|---|---|---|
| 3,947,453 | 3/1976 | Jones | 260/287 |
| 4,762,720 | 8/1988 | Jizomoto | 424/450 |
| 5,019,394 | 5/1991 | Hamaguchi et al. | 424/423 |
| 5,034,228 | 7/1991 | Meybeck et al. | 424/401 |
| 5,080,904 | 1/1992 | Iga et al. | 424/450 |
| 5,116,606 | 5/1992 | Alt | 424/70 |
| 5,133,958 | 7/1992 | Stuckler | 424/61 |

FOREIGN PATENT DOCUMENTS

| | | |
|---|---|---|
| 318369 | 5/1989 | European Pat. Off. |
| 2556968 | 6/1985 | France . |
| 2661090 | 10/1991 | France . |
| 39933 | 11/1986 | Hungary . |
| 02304009 | 12/1990 | Japan . |
| 96962 | 5/1989 | Romania . |
| 678487 | 9/1991 | Switzerland . |
| 1604839 | 11/1990 | U.S.S.R. . |

OTHER PUBLICATIONS

Yasugawa et al., *Nihon Univ. J. Med.*, 31(4), pp. 229–234, (1989).
Kojima et al. *Phytochemistry*, 29(7), pp. 2351–2355, (1990). Abstract only.
Dmitruk et al. *Rastit. Resur.*, 21(4), pp. 463–469, (1985). Abstract only.
Lubica et al., *Acta Fac. Pharm.*, 21, pp. 33–61, (1972). Abstract only.
Kojima et al. *Phytochemistry* vol. 25(3), pp. 729–733, (1986).
Kojima et al. *Phytochemistry* vol. 26(4), pp. 1107–1111, (1987).
Kojima et al. *Phytochemistry* vol. 27(9), pp. 2921–2925, (1988).
Tabba et al. *Antiviral Research* vol. 11, pp. 263–274, (1989).
Yao et al. *Virology* vol. 187, pp. 56–62, (1992).
Lin et al. *Mutation Research*, vol. 204, pp. 229–234, (1988).
WPIL, Serveur de Bases de Donnees, AN–91–033705 [05], Derwent Publications Ltd, Londres, GB, & JP,A,2304009 (Pola Chem. Inc. K.K.) 17 Dec. 1990.
Parfums, Cosmetiques, Aromes, No. 69, juin–juillet 1986, (Paris, FR), O. Schmidger: "Extraits vegetaux: produits cosmetiques et phytopharmaceutiques", pp. 51–54.
Patent Abstracts of Japan, vol. 13, No. 315 (C–619), 18 Jul. 1989.
Patent Abstracts of Japan vol. 11, No. 300 (C–449), 29 Sep. 1987.

*Primary Examiner*—Ralph J. Gitomer
*Assistant Examiner*—Howard C. Lee
*Attorney, Agent, or Firm*—Popham, Haik, Schnobrich & Kaufman, Ltd.

[57] ABSTRACT

The invention relates to the use of an extract of prunella or at least one prunella saponin. This extract or this saponin is used for the preparation of a cosmetic or pharmaceutical and/or dermatological composition. Said composition makes it possible to regulate the renewal and differentiation of the keratinocytes and has an anti-aging activity, an anti-inflammatory activity, especially in inflammations caused by ultraviolet radiation, or an anti-allergic or anti-free-radical activity. It also enables the epidermis of normal skin to be kept in good condition, especially by maintaining the functional role of the skin, in particular as a protective barrier, and makes it possible to prevent or treat dry skin, especially ichthyotic skin, and to treat psoriasis.

18 Claims, 1 Drawing Sheet

COSMETIC OR PHARMACEUTICAL COMPOSITION CONTAINING A PRUNELLA EXTRACT

The present invention relates essentially to a cosmetic or pharmaceutical composition, especially dermatological composition, containing an extract of prunella.

More precisely, the present invention relates to the use of an extract of prunella or at least one prunella saponin for the preparation of a cosmetic or pharmaceutical composition, especially dermatological composition, having in particular an anti-inflammatory, anti-allergic or anti-aging activity, promoting or regulating the renewal of skin cells, for preventing and treating hair loss or alopecia, and to a cosmetic composition for the application thereof.

The plants of the genus Prunella, in particular *Prunella vulgaris* L or "milfoil" also known as common prunella or comfrey, are common Labiatae in countries of the temperate zone, especially France. Conventionally, it was used fresh, with its sap, especially in the form of a gargle for treating sore throats and coughs.

It has also been used as an infusion to treat hemorrhages and diseases of the digestive tract. An antimutagenic activity of extracts of *Prunella vulgaris* L. has been described more recently by Lee and Lin in Mutation Research, 204 (1988), 229–234.

It is known that the effects of aging on the skin are characterized in particular by a slowing-down of the cell differentiation in the skin, resulting in a slowing-down of the renewal of the cells, their activity and their morphology, and a slowing-down of the transformation of the keratinocytes to corneocytes, giving the skin a duller, dried and more wrinkled appearance. Ageing also has adverse effects on the hair follicles. The cells of the follicles, like those of the epidermis, have their activity reduced by said effects, resulting in a slowing-down of the growth of the hair and, ultimately, degeneration of the follicle and the definitive loss of the hair.

One main object of the present invention is therefore to solve the novel technical problem which consists in providing a novel formulation of a cosmetic or pharmaceutical composition, especially dermatological composition, having a good efficacy in renewing the epidermis, renewing hair growth and preventing or slowing down hair loss, and in combating the effects of ageing on the condition of the skin, hair and nails.

A further main object of the present invention is to solve the novel technical problem which consists in providing a novel formulation of a cosmetic or pharmaceutical and/or dermatological composition having an anti-inflammatory activity, in particular on the erythema caused by ultraviolet radiation.

A further main object of the present invention is to solve the novel technical problem which consists in providing a novel formulation of a cosmetic or pharmaceutical composition, especially dermatological composition, having an anti-allergic activity.

A further main object of the present invention is to solve the above-mentioned novel technical problems in a particularly simple manner which does not necessarily require the isolation of a particular active substance or its synthesis, which is satisfactory and which can be used on the industrial scale.

Thus, according to a first feature, the present invention relates to the use of an extract of prunella or at least one prunella saponin for the preparation of a cosmetic or pharmaceutical composition, especially dermatological composition, regulating the renewal and differentiation of the keratinocytes, said composition having an anti-inflammatory activity, especially in inflammations caused by ultraviolet radiation, or an anti-allergic or anti-free-radical activity, for improving the functional condition of the skin or keeping it in a good functional condition, for preventing or treating dry skin, especially ichthyotic skin, and for treating psoriasis.

In one particularly preferred variant, the. above-mentioned prunella is *Prunella vulgaris* L. or common prunella.

In one particular variant, the above-mentioned extract of prunella or the above-mentioned prunella saponin is obtained by extraction from the whole plant or, preferably, from the aerial parts of prunella. Particularly preferably, those parts of the plant which are used are dried prior to the extraction treatment.

In particular, the above-mentioned extract of prunella can be obtained by the process described below by way of indication, but without implying a limitation. The dry matter, preferably consisting of aerial parts of prunella, is subjected to a primary extraction with a solvent selected from the group consisting of water, alcohols preferably containing from 1 to 4 carbon atoms, chlorinated solvents preferably containing 1 or 2 carbon atoms, organic esters preferably containing from 3 to 6 carbon atoms, or a mixed solvent based on any mixture of the above-mentioned solvents.

Advantageously, the primary extraction solvent is water, methanol, ethanol, a methanol/water mixture or an ethanol/water mixture, chloroform or dichloromethane, preferably water or methanol.

The ratio of plant material to extraction agent is not critical and will generally be between 1:5 and 1:20 parts by weight.

The above-mentioned primary extraction is carried out at temperatures between room temperature and the boiling point of the solvent used for the extraction.

The primary extraction is preferably carried out under reflux at atmospheric pressure for a period of 2 to 4 h. In addition, it is advantageously preceded by maceration in the cold for 2 to 4 h in the extraction solvent.

When the extraction is complete, the solvent phase containing the extract is filtered and then concentrated and/or evaporated to dryness under reduced pressure to give a first extract of prunella according to the invention.

In one particular variant, the use according to the invention relates to a mixture of prunella saponins. A mixture of prunella saponins according to the invention is obtained in particular from the above-mentioned first extract of prunella, concentrated or dry, by following the procedure indicated below. The above-mentioned first extract is introduced into and then agitated in an apolar solvent which is preferably miscible with the primary extraction solvent, such as a low-molecular ether or ketone, in particular ethyl or isopropyl ether, acetone or methyl ethyl ketone. The amount of apolar solvent by weight is generally 5 to 100 parts per part of primary extract. The insoluble material and/or the precipitate formed contains mainly a mixture of saponins according to the invention.

Advantageously, the mixture of saponins obtained above is purified by any process accessible to those skilled in the art.

In particular, the above-mentioned insoluble material and/or precipitate is redissolved in about 20 times its own weight of water. The aqueous solution is then extracted 3 to 4 times with a sparingly water-soluble alcohol such as butanol, saturated with water, for example in proportions of 1/1 by volume for each extraction operation. The alcoholic phases are pooled and evaporated under reduced pressure. The residue is dissolved in about 10 times its own weight of water and the solution is then dialyzed against pure water for 4 to 5 days. The contents of the dialysis cell are lyophilized. The purification of the mixture of saponins obtained can optionally be further improved by dissolving the lyophilizate in methanol and then discharging the solution into ethyl ether. The precipitate formed is collected.

According to a second feature, the present invention further relates to a cosmetic or pharmaceutical composition, especially dermatological composition, having an anti-inflammatory or anti-allergic activity or an inhibitory activity on the erythema caused by UV radiation, said composition comprising, as the active ingredient, a cosmetically or pharmaceutically effective amount of an extract of prunella or at least one prunella saponin, if appropriate in a cosmetically or pharmaceutically acceptable excipient.

In another embodiment, the invention relates to a cosmetic or pharmaceutical composition, especially dermatological composition, regulating the renewal and differentiation of the keratinocytes, for combating aging of the skin or for improving the functional condition of the skin or keeping it in a good functional condition, in particular as a protective barrier, said composition comprising, as the active ingredient, a cosmetically or pharmaceutically effective amount of an extract of prunella or at least one prunella saponin, if appropriate in a cosmetically or pharmaceutically acceptable excipient.

In yet another embodiment of the invention, the latter relates to a cosmetic or pharmaceutical composition, especially dermatological composition, having an anti-free-radical activity, said composition comprising, as the active ingredient, a cosmetically or pharmaceutically effective amount of an extract of prunella or at least one prunella saponin, if appropriate in a cosmetically or pharmaceutically acceptable excipient.

In another embodiment, the invention further relates to a cosmetic or pharmaceutical composition, especially dermatological composition, for preventing or treating dry skin, especially ichthyotic skin, said composition comprising, as the active ingredient, a cosmetically or pharmaceutically effective amount of an extract of prunella or at least one prunella saponin, if appropriate in a cosmetically or pharmaceutically acceptable excipient.

The present invention further relates to a pharmaceutical composition, especially dermatological composition, for treating psoriasis, said composition comprising, as the active ingredient, a pharmaceutically effective amount of an extract of prunella or at least one prunella saponin, if appropriate in a pharmaceutically acceptable excipient.

In another advantageous variant of the invention, the cosmetic or pharmaceutical composition, especially dermatological composition, according to the invention also comprises an effective concentration of at least one other active substance selected from xanthines, vitamins, in particular vitamins A, B and E, or derivatives thereof, for example vitamin A esters, tyrosine or derivatives thereof, for example glucose tyrosinate and malyltyrosine, quinine or derivatives thereof, rubefacients such as methyl nicotinate, a papilla fibroblast culture supernatant as described in the document EP-A-272 920, keratin hydrolyzates, trace elements such as zinc, selenium and copper, a bisbenzylisoquinoline alkaloid such as oxyacanthine or cepharanthine, 5-α-reductase inhibitors such as progesterone, cyproterone acetate and minoxidil 6-Piperidino-2,4-diaminopyrinidine 3-oxide, azelaic acid and derivatives thereof, a 1,4-dimethyl-4-azasteroid, in particular 17-β-N,N-diethylcarbamoyl-4-methyl-4-aza-5-α-androstan-3-one, or else an extract of Serenoa repens.

The cosmetic or pharmaceutical compositions, especially dermatological compositions, according to the present invention, in particular those presented in the form of creams, milks, gels or lotions, can be applied topically for regulating the renewal and differentiation of the keratinocytes, for combating the effects of aging on the condition of the skin, for improving the functional condition of the skin or keeping it in a good functional condition, for preventing or treating dry skin or for treating psoriasis.

According to this feature, the present invention also provides a method of treating aging of the epidermis, inflammation, solar erythema, skin allergies or the disorder caused by the action of free radicals, for improving the functional condition of the skin or keeping it in a good functional condition, for preventing or treating dry skin or for treating psoriasis, said method comprising the topical application, in an effective amount for achieving said desired effect, of at least one extract of prunella or at least one prunella saponin, if appropriate incorporated in a cosmetically or pharmaceutically acceptable excipient.

According to another feature, the invention also provides a process for the manufacture of a cosmetic or pharmaceutical composition, especially dermatological composition, regulating the renewal and differentiation of the keratinocytes, said composition having an anti-aging activity, an antiinflammatory activity, especially in inflammations caused by ultraviolet radiation, or an anti-allergic or anti-free-radical activity, for improving the functional condition of the skin or keeping it in a good functional condition, for preventing or treating dry skin, especially ichthyotic skin, and for treating psoriasis, said process comprising the use of at least one extract of prunella or at least one prunella saponin, which is mixed with a pharmaceutically or cosmetically acceptable excipient, vehicle or carrier.

In all the foregoing features, the concentration of extract of prunella or prunella saponin is advantageously between 0.001% and 5% by weight of the total composition.

The proportions indicated in the description and in the claims are by dry weight in the case of plant extracts.

In all the foregoing features, in one particularly advantageous variant of the invention, the cosmetic or pharmaceutical composition, especially dermatological composition, according to the invention can also contain hydrated lipidic lamellar phases or liposomes, which may or may not incorporate the extract of prunella defined above.

The term "lipidic" in the expression "lipidic lamellar phase" covers all substances which comprise a so-called fatty hydrocarbon chain generally containing more than 5 carbon atoms, this substance usually being called a "lipid".

According to the invention, the lipids used to form the lipidic lamellar phase or the liposome-type vesicles are amphiphilic lipids, i.e. lipids consisting of molecules possessing either an ionic or a non-ionic hydrophilic group and a lipophilic group, these amphiphilic lipids being capable of forming a lipidic lamellar phase or liposome-type vesicles in the presence of an aqueous phase, depending on the amount of water in the mixture.

The following may be mentioned in particular among these lipids: phospholipids, phosphoaminolipids, glycolipids, polyoxyethylenated fatty alcohols and optionally polyoxyethylenated polyol esters. Such substances consist for example of an egg or soya lecithin, a phosphatidylserine, a sphyngomyelin, a cerebroside, a glycosylceramide or an oxyethylenated polyglycerol stearate.

It is preferable according to the invention to use a mixture of lipids consisting of at least one amphiphilic lipid and at least one hydrophobic lipid such as a sterol like cholesterol or beta-sitosterol. The amount of hydrophobic compounds, expressed by weight, must not generally exceed the amount of amphiphilic lipids and preferably must not exceed 0.5 times this amount.

In one preferred variant, the above-mentioned extract of prunella or saponin is introduced into the aqueous phase of the hydrated lipidic lamellar phase or of the liposomes in a concentration between 0.001% and 5% by weight of the total weight of said aqueous phase.

In yet another preferred variant, the above-mentioned extract of prunella or saponin is at least partially incorporated into the lipidic phase of the hydrated lipidic lamellar phase or of the liposomes in a concentration preferably between 0.01% and 30% by weight of said lipidic phase and particularly preferably between 0.01% and 10% by weight of this phase.

It is pointed out that the expression "at least partially incorporated" covers the case where the substance is totally incorporated and the case where only a certain amount of this substance is incorporated.

The above-mentioned saponin or corresponding sapogenin or the extract of prunella according to the invention can be incorporated into hydrated lipidic lamellar phases or into liposomes by the known preparative techniques, for example those described in the document EP-B1-0 087 993=U.S Pat. No. 4,508,703, if appropriate in combination with the document EP-B1-0-101-599=U.S. Pat. No. 4,621,023.

In one variant of the above-mentioned manufacturing process, the latter comprises firstly the addition of hydrated lipidic lamellar phases or of liposomes to an extract of prunella or to the prunella saponin, with or without incorporation of said extract of prunella or said prunella saponin into said phases or into said liposomes, and secondly the addition of the resulting mixture to a pharmaceutically or cosmetically acceptable excipient, vehicle or carrier.

Other objects, characteristics and advantages of the invention will become clearly apparent from the following explanatory description referring to several Examples, which are given solely by way of illustration and consequently cannot in any way limit the scope of the invention.

The percentages are expressed by weight in the Examples, unless indicated otherwise. In the case of extracts, their amounts are expressed by dry weight.

BRIEF DESCRIPTION OF THE DRAWINGS

The FIGURE shows the results of a trichokinetic study described in Example 7. The FIGURE shows the percentage of hairs in the anagenic phase (growth phase) as a function of time in Sprague Dawley rats undergoing treatment with compositions of the present invention.

EXAMPLE 1

Preparation of a methanolic extract of prunella

About 500 g of leaves of *Prunella vulgaris* L. or common prunella, dried in air and powdered, are macerated for about 2 h in 1.2 1 of methanol. The mixture is refluxed for 3 h. After cooling, the solution is filtered on a no. 3 glass frit. The residues are re-extracted in the same way with 2 times 1 1 of methanol. The three filtrates are pooled and concentrated on a rotary evaporator.

This gives a methanolic extract of prunella according to the invention. If desired, a dry extract can be obtained by heating the above extract to constant weight in an oven at between about 40° C. and 60° C.

EXAMPLE 2

Preparation of a suspension of gelled liposomes containing an extract of prunella 9 g of soya lecithin, 1 g of β-sitosterol and 1 g of dry extract of prunella prepared according to Example 1 are dissolved in 100 ml of a 9:1 chloroform/methanol mixture.

The solution is evaporated under reduced pressure at 60° C. on a rotary evaporator by Bangham's method, which is well known to those skilled in the art in the field of liposomes, until a lipidic film is deposited on the inner surface of the flask.

89 g of distilled water are then introduced into the flask. The flask is agitated until the lipidic film has completely dispersed in the water at room temperature, which generally requires at least 2 to 4 h of agitation in practice, and the dispersion is then homogenized with ultrasound at 4° C. for 10 min at a power of 150 W.

The liposomes obtained have a mean size of about 100 nm.

This suspension of liposomes is preferably gelled by being mixed with 100 g of a 1.25% gel of Carbopol 940® separately prepared in conventional manner. This gives about 200 g of a gelled suspension of liposomes incorporating the bulk of the above-mentioned extract of prunella. The concentration of this extract is about 0.5%, based on the total weight of the gelled suspension.

It can be seen that by performing various dilutions, it is possible to obtain compositions containing variable proportions of extracts of prunella, which constitutes a particularly easy mode of formulation.

EXAMPLE 3

Test for activity on the renewal of the epidermis

In Petri dishes of diameter 35 mm, 50,000 transformed human keratinocytes are inoculated into 2 ml of EMEM from Gibco, which has been complemented with 1% by volume of FCS (FCS =fetal calf serum) but no antibiotic.

Incubation is carried out for 24 h at a temperature of 37° C.

After these 24 h of incubation, the media are renewed with a medium which is identical but respectively contains different concentrations of the test products, as defined below. The tests are performed in triplicate and control dishes are provided which contain only the solvent for the test product.

Incubation is carried out for 5 d at a temperature of 37° C. under an atmosphere of air containing 5% of $CO_2$.

After these 5 d of incubation, the cells are detached with trypsin and counted using an apparatus known as a Coulter Cowter.

The test product is a crude methanolic extract of *Prunella vulgaris* according to Example 1, solubilized in DMSO.

This product is introduced into the culture medium in different concentrations ranging from 1 μg to 10 μg (dry extract) per milliliter of culture medium.

The results obtained are listed in Table I, which indicates the mean number of cells per dish after the 5 d of incubation and, for the treated dishes, the activity A of the test products calculated from the number of cells in each category of dish:

$$A = \frac{\text{treated dishes} - \text{control dishes}}{\text{control dishes}} \times 100$$

A statistical study showed that the differences between the number of cells in the treated dishes and the control dishes, after incubation, were all significant.

TABLE 1

| Concentration of extract of the invention, Example 1 (µg/ml) | Number of cells per dish × $10^3$ | Activity A % | Significance |
|---|---|---|---|
| DMSO control | 90 ± 13 | 0 | |
| 1 | 134 ± 23 | +49 | S |
| 2.5 | 173 ± 2 | +92 | S |
| 10 | cytotoxic | | |

EXAMPLE 4

Demonstration of the inhibition of phospholipase $A_2$ (or $PLA_2$)

The inhibition of phospholipase $A_2$ is measured, phospholipase $A_2$ being involved in the production of allergy and inflammation mediators, especially in the inflammatory reactions of skin allergies, according to the protocol described by H. W. Chang, I. Kudo, M. Tomita and K. Inoue in J. Biol. Chem., 1987, 102, 147–154.

Phospholipase $A_2$ is isolated from mouse peritoneal fluid. Phospholipase $A_2$ hydrolyzes, in the 2position of the glycerol, a phosphatidylethanolamine radiolabeled with carbon 14; this releases a fatty acid, which will be determined by liquid scintillation. With an inhibitor of this enzyme, the hydrolysis will be reduced and less fatty acid will therefore be determined.

In practice, the phospholipase $A_2$ and the test extract are placed in a 0.1 M Tris buffer, pH =9, containing 4 mM $Ca^{2+}$ and incubation is carried out for 40 min at 37° C. After this contact time, the labeled substrate is added and incubation is continued for 40 min at 37° C to enable hydrolysis of the substrate to take place. The fatty acid is then extracted with an organic phase of n-heptane and counted by liquid scintillation. The 50% inhibitory concentration ($IC_{50}$), for which 50% of the enzyme is inhibited, is then determined.

A 50% inhibitory concentration of 17 µg/ml is thus obtained with the methanolic extract of prunella according to Example 1, demonstrating that this extract of prunella has a very good inhibitory activity on phospholipase $A_2$.

The same test performed with an aqueous extract of prunella gives an $IC_{50}$ of 28 µg/ml.

EXAMPLE 5

Anti-inflammatory activity of an extract of prunella on the erythema caused by ultraviolet This is investigated using 41 female Dunkin Hartley guinea-pigs weighing 400 to 450 g, divided into 6 groups of 6 and one group of 5 guinea-pigs.

For one week before the start of the experiment, the animals are kept at a temperature of 20° plus or minus 1° C. and at a hygrometry of 50% plus or minus 10% and with 12 h of light per day. On the day before the experiment, the animals are carefully shaved on the back using an AESCULAP shaver equipped with a 1/10 mm comb, and then shaved gently on both sides using a Braun razor. A depilating cream is subsequently applied (to a thickness of about 2 mm) and allowed to work for 15 min.

The cream is removed with a wooden spatula and the guinea-pigs are then rinsed with tepid water and dried.

The guinea-pigs then receive the same irradiation on both sides, the area of the irradiated regions being 2 $cm^2$. The right side receives the test product, the product being spread beyond the 2 $cm^2$ so as to make it possible to observe any redness which might be due to the product and which would mask an antiphlogistic effect. The left side receives the placebo.

Application of the placebo to the left side enables the effect of UV to be measured under the same conditions on the zones treated with the product and on the untreated zones. This also makes it possible to see any action of the placebo and to assess, in comparison with the placebo, the zone to which the product has been applied.

The products are applied immediately after irradiation and then every 2 h up to 6 h after irradiation.

The amount applied is not measured but is spread uniformly over the whole region (about 1 mg).

The irradiation device used consists of a Biotronic UV312-365 mercury lamp (Vilbert-Loumat). The device for measuring the UV energy, which consists of a photoelectric cell measuring the luminous power of the UV, is fixed to a support at the center of the irradiated zone. This cell is connected to a radiometer on which the desired energy—in this case 2.16 $J/cm^2$ of UVB (distance from guinea-pig to lamp=20 cm)—is programmed. The lamp switches off automatically once the total amount of energy has been emitted.

This irradiation causes an erythema equal to 3 plus or minus 0.5 (see scale) at 6 h.

20 min before irradiation, the animals are anesthetized with an intraperitoneal dose of 0.5 ml/kg of pentobarbital sodium.

Six hours after irradiation, the erythema in each region is evaluated macroscopically according to the following scale:

0 ............... no erythema
1 ............... slight but visible erythema
2 ............... clearly visible erythema
3 ............... substantial erythema One guinea-pig with a score of 1 according to the above notation, one guinea-pig with a score of 2 and one guinea-pig with a score of 3 are singled out after having been thoroughly evaluated as such, and are taken as standard references so that half-unit scores can be awarded. A guinea-pig not evaluated with 1 (standard reference) and not evaluated with 2 will be given a score of 1.5.

The results are shown in Table II.

The results of the difference (UV+placebo)−(UV+product) are shown in Table II bis.

The results obtained are used to calculate the percentage activity according to the following formula:

$$\text{percentage activity} = \frac{\overline{X}(\text{control UV} + \text{placebo}) - \overline{X}(\text{UV product})}{\overline{X}(\text{control UV} + \text{placebo})} \times 100$$

TABLE II

| | Aqueous extract of prunella in aqueous gel | | Methanolic extract of Example 1 in ethanolic gel | | Indomethacin in hydrocerine | |
|---|---|---|---|---|---|---|
| Score | placebo | product | placebo | product | placebo | product |
| 1 | 3 | 1.5 | 3 | 1.5 | 3 | 0.5 |
| 2 | 2.5 | 2.5 | 2.5 | 1 | 3 | 1 |
| 3 | 2.5 | 1.5 | 2.5 | 1.5 | 3 | 0 |

TABLE II-continued

| | Aqueous extract of prunella in aqueous gel | | Methanolic extract of Example 1 in ethanolic gel | | Indomethacin in hydrocerine | |
|---|---|---|---|---|---|---|
| Score | placebo | product | placebo | product | placebo | product |
| 4 | 2 | 1 | 3 | 1.5 | 3 | 0 |
| 5 | 2 | 1.5 | 2.5 | 1.5 | 2.5 | 0.5 |
| 6 | 2.5 | 1.5 | 2.5 | 1 | | |
| mean | 2.41 | 1.58 | 2.66 | 1.33 | 2.9 | 0.4 |
| standard deviation | 0.37 | 0.49 | 0.25 | 0.26 | 0.22 | 0.41 |
| protection | 34.4% | | 50% | | 86.2% | |
| Student t | 3.95 | | 12.64 | | 11.18 | |
| | > ** | | > *** | | > *** | |

> **significant at 1%
> ***significant at 0.1%

TABLE II bis

| Score | Aqueous extract of prunella in aqueous gel | Methanolic extract of Example 1 in ethanolic gel | Indomethacin in hydrocerine |
|---|---|---|---|
| 1 | 1.5 | 1.5 | 2.5 |
| 2 | 0 | 1.5 | 2 |
| 3 | 1 | 1 | 3 |
| 4 | 1 | 1.5 | 3 |
| 5 | 0.5 | 1 | 2 |
| 6 | 1 | 1.5 | |
| mean | 0.83 | 1.33 | 2.5 |
| standard deviation | 0.52 | 0.26 | 0.5 |

Thus it is found that the extracts of prunella according to the present invention have an activity of 34.4% or 50%, which is to be compared with the 86.2% activity of indomethacin acting as positive control.

It will be seen that the products of the invention thus exhibit a good antiphlogistic activity under the experimental conditions, thereby avoiding the need to use products such as indomethacin, which were previously necessary for obtaining a satisfactory activity.

The tested extracts according to the invention are in a concentration of 0.2% by weight in the gel. The indomethacin is in a concentration of 1% in the hydrocerine.

EXAMPLE 6

Activity on the differentiation of the keratinocytes

A number of modifications appear in the keratinocytes in the course of aging. First of all, it should be pointed out that the keratinocytes are not a totally homogeneous population, but rather a mozaic of cells. In ultrastructural terms, the literature makes the following distinction:

a) Intrinsic aging

The corneal layer is thickened, the corneocytes are less adherent and there seems not to be a very substantial quantitative and qualitative modification of the tonofilaments, the keratinohyalin granules and the cell organelles.

b) Actinic aging

The intercellular spaces are enlarged, intracytoplasmic vacuoles are present, the tonofilaments are shorter and have a mesh-like distribution, a variable number of the desmosomes are degraded and there is a reduction in the microvilli.

For the present study, a skin sample was taken during esthetic surgery of the face-lift type on the face of a 42-year-old woman.

A culture of keratinocytes isolated from this sample was prepared in conventional manner in six Petri dishes. Three of them are treated with the methanolic extract of prunella of Example 1 at a non-cytotoxic dose of 0.25 µg/ml, the other three remaining untreated.

The cultures of keratinocytes, respectively treated with the extract of prunella according to Example 1 and untreated (control), are included in a resin; a section of each of it is then prepared and observed under a transmission electron microscope. The results of this observation are listed in Table III below.

TABLE III

| | Control | Extract of prunella, Example 1 |
|---|---|---|
| Upper layer | signs of degeneration no corneal envelope no keratohyalin granules, or these are important for keratinization | corneal layer ++ many keratohyalin granules fewer organelles 2 to 3 layers of keratinization |
| Intermediate layer | a few tonofilaments large intercellular spaces a few desmosomes | a very large number of highly differentiated desmosomes many tonofilaments |
| Basal layer | a few hemidesmosomes | a large number of desmosomes |

Table III above shows that a highly differentiated culture is obtained with the extract of prunella according to the present invention, demonstrating that the extract of prunella has a highly significant antiaging activity and regulatory activity on the differentiation of the keratinocytes.

Also, because of the effect of normalizing the differentiation of the keratinocytes, the compositions according to the invention enable the epidermis of "normal" skin to be kept in good condition, especially by maintaining its suppleness and its functional role, in particular as a protective barrier.

The compositions of the invention can be used for preventing or treating dry skin, especially ichthyotic skin.

The invention can also be used for treating psoriasis.

It should in fact be pointed out that the phenomena of dry skin and psoriasis are accompanied by a keratinocyte differentiation disorder. In particular, the psoriatic keratinocytes are poorly developed and immature, the number and size of the tonofilaments are degraded and certain cells in the corneal layer still contain organelles, or even a nucleus, showing that differentiation has not taken place correctly.

In the case of dry skin, in particular ichthyosis, the differentiation of the keratinocytes is imperfect, being accompanied by malformations of the keratohyalin granules and the desmosomes. The epidermis exhibits abnormal keratinization, resulting in a perturbation of the barrier properties and a loss of elasticity.

EXAMPLE 7

Demonstration of the activity of the products of the invention on the pilary system The test is based on a study of the activity of the products according to the invention on the pilary cycle of Sprague Dawley rats, all of which are 23 d old (d =day). The pilary cycles of all the animals are still synchronous at this age.

The aim is more particularly to demonstrate the action of the test products on the prolongation of the hair growth phase or so-called "anagenic phase".

This is done in the following manner. On d 24, all the rats are shaved on the sides of the lower part of the back so as to leave only a short length of hair which is just enough to allow subsequent depilation.

From d 25 (age of the rats) to d 65, the test products are then applied, 6 d out of 7, at a dose which changes with the weight of the animals. This dose is 0.5 ml on d 25 and reaches 2 ml on d 65.

At substantially regular intervals of time (about every 3 d), starting from d 28, a tuft of hairs is removed from the animal's left side using tweezers. The roots of 10 hairs selected at random from this tuft are observed under high magnification and the number of hairs in the anagenic phase, recognizable by the characteristic shape of the root, is counted. The percentage of hairs in the anagenic phase (growth phase) is thus determined as a function of time on groups of 10 animals.

The study is performed on 30 rats divided into 3 groups of 10 animals. The first group receives a preparation according to the invention having the following composition (composition "T"):

| | |
|---|---|
| extract of prunella according to Example 1 | 0.1 g |
| cepharanthine | 0.1 g |
| propylene glycol | 20.0 g |
| distilled water | 15.0 g |
| 95% ethyl alcohol qsp | 100.0 g |

The second group receives only the above-mentioned excipient. The third group is the control group, which does not receive any product.

Figure 1:
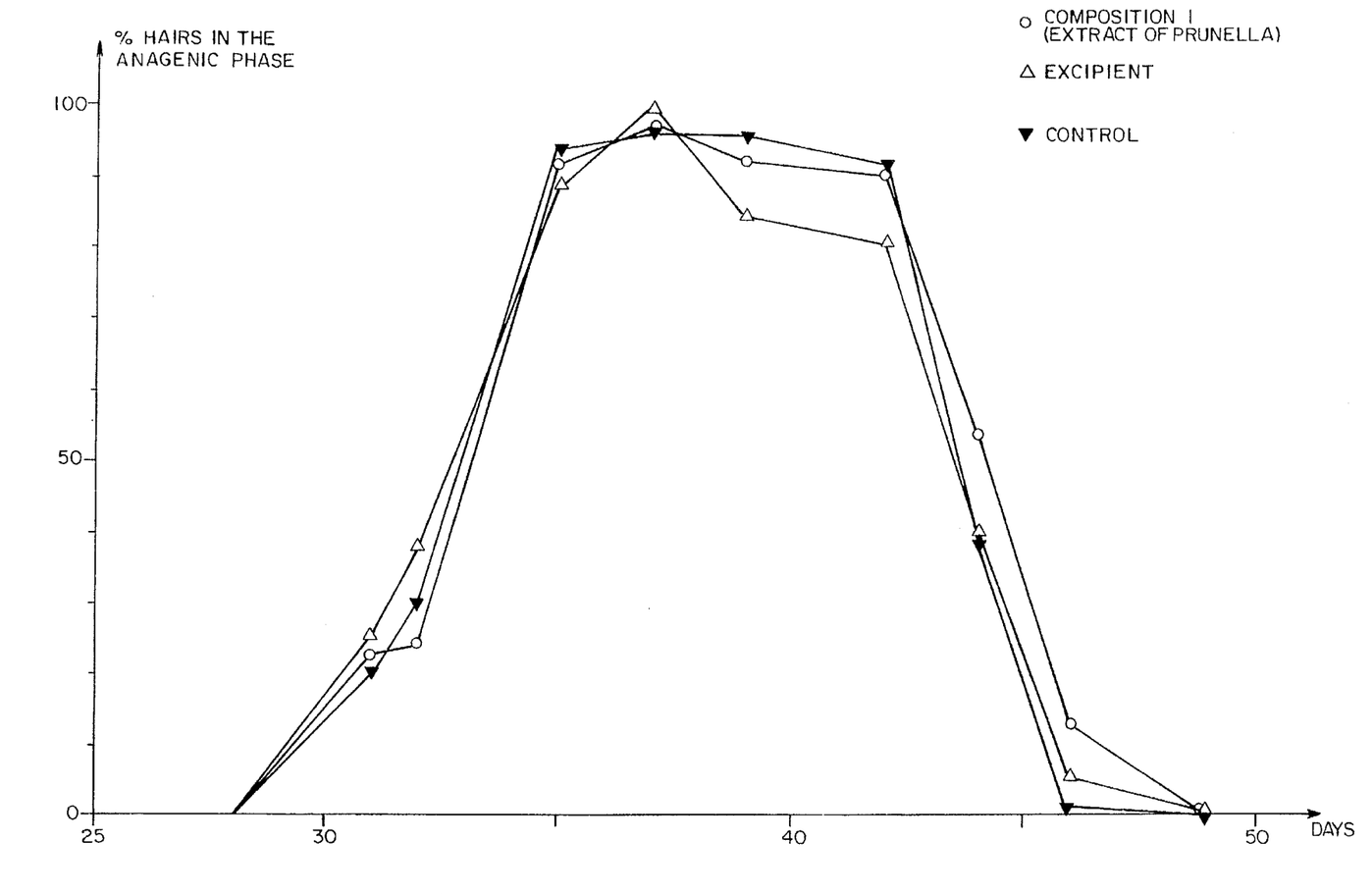

The results of this trichokinetic study (trichogram as a function of time) are shown as mean values in Table IV and represented in the single Figure attached.

TABLE IV

| | Percentage of anagenic hairs | | | | | | | | | |
|---|---|---|---|---|---|---|---|---|---|---|
| | 28 d | 31 d | 32 d | 35 d | 37 d | 39 d | 42 d | 44 d | 46 d | 49 d |
| Composition "T" (invention) | 0 | 23 | 24 | 92 | 96 | 92 | 90 | 53 | 13 | 0 |
| Excipient only | 0 | 26 | 38 | 88 | 98 | 83 | 80 | 40 | 5 | 0 |
| Control | 0 | 21 | 30 | 93 | 96 | 95 | 91 | 38 | 1 | 0 |

In this Figure, the percentage of hairs in the anagenic phase has been shown on the ordinate and the age of the animals, expressed in days, has been shown on the abscissa.

The curve joining the circles corresponds to the results obtained with the preparation according to the invention (composition "T"), the curve joining the upward-pointing triangles is obtained with the excipient and, finally, the curve joining the downwardpointing triangles is obtained with the control group, which does not receive any product.

It is seen that the anagenic phase is more prolonged in the rats treated with the product according to the invention, especially in comparison with the rats treated with the excipient only. This is particularly marked from d 37 onwards.

Thus it is clear that, by extending the duration of the anagenic phase, the extracts of prunella according to the invention very substantially retard hair loss and promote renewed growth.

Various Examples of formulations of cosmetic or pharmaceutical compositions promoting renewed hair growth and/or retarding hair loss and/or promoting or regulating the renewal or growth of the epidermis will be given below.

EXAMPLE 8

0.2 g of an extract of prunella obtained by extraction with water according to a procedure similar to that described in Example 1 is dissolved in 49.2 g of distilled water and this solution is then gelled by the addition of 50 g of a neutralized 3% gel of Carbopol 940®.

This gel can be applied twice a day in a 4-month course of treatment.

EXAMPLE 9

Lotion for combating the loss of hair follicles, in particular on the scalp

The following composition is prepared:

| | |
|---|---|
| extract of prunella according to Example 1 | 0.1 g |
| panthenol | 0.1 g |
| keratin hydrolyzate | 0.3 g |
| perfume | 0.1 g |
| 40% alcohol qsp | 100 g |

EXAMPLE 10

Styling gel for combating hair loss

The following composition is prepared in a manner well known to those skilled in the art:

| | |
|---|---|
| extract of prunella according to Example 1 | 0.2 g |
| neutralized 1.50% gel of Carbopol 940 ® | 45 g |
| Phytantriol ® | 0.1 g |
| Crémophor RH40 ® | 0.5 g |
| protein/zinc complex | 0.1 g |
| preservative | 0.05 g |
| perfumed aqueous excipient qsp | 100 g |

The gel obtained is applied in the morning and evening for 6 months to the areas where hair follicles are being lost.

EXAMPLE 11

Treating gel for combating seborrheic alopecia

The following composition is prepared:

| | |
|---|---|
| extract of prunella according to Example 1 | 0.2 g |
| Crémophor RH40 ® | 0.5 g |
| perfume | 0.1 g |
| protein/zinc complex | 0.05 g |
| 1.50% Carbopol 940 ® gel | 45 g |
| aqueous excipient qsp | 100 g |

This gel can be applied to the hair in the morning and evening for 6 months.

EXAMPLE 12

Treating cream for combating cutaneous senescence

A cream containing 0.2% of an extract of prunella is prepared in the following manner:

| | |
|---|---|
| Composition A (percentage by weight) | |
| Tefosse 1500 ® from Gattefossé | 7.00 |
| cetyl alcohol | 2.00 |
| Primol 352 ® from ESSO | 25.00 |
| Composition B (percentage by weight) | |
| demineralized water | 54.40 |
| Carbopol 940 ® from Polyplastic | 0.30 |
| triethanolamine | 0.30 |
| Composition C (percentage by weight) | 0.80 |
| Germaben II ® from Seppic | |
| Composition D (percentage by weight) | |
| demineralized water | 10.00 |
| aqueous extract of prunella (dry extract) | 0.20 |

Composition A is heated to 75° C. and the Carbopol 940® is then dispersed in the water of composition 10 B. The gel is neutralized with the triethanolamine. Solution B is heated to 75° C. An emulsion of composition A in composition B is produced at 75° C. and then cooled to 40° C., with stirring.

Composition C is then added. The components of composition D are premixed and composition D is then added to the formulation. The product is homogenized and cooled to room temperature to give a cream.

This cream can be applied twice a day in a 6-month course of treatment to give regenerated supple skin.

EXAMPLE 13

Gel for treating psoriasis

| | |
|---|---|
| extract of prunella according to Example 1 | 0.15 g |
| 1.5% Carbopol 980 ® gel | 48. g |
| aqueous excipient qsp | 100. g |

Use by local application twice a day for 12 weeks.

EXAMPLE 14

Emulsion for dry skin

| | |
|---|---|
| extract of prunella according to Example 1 | 0.05 g |
| hyaluronic acid | 1. g |
| glycerol | 1. g |
| excipient for oil-in-water emulsion, qsp | 100. g |

Apply this cream for 6 weeks to the dry areas of the skin.

EXAMPLE 15

Emulsion for dry skin

| | |
|---|---|
| extract of prunella according to Example 1 | 0.15 g |
| excipient for water-in-oil emulsion, qsp | 100. g |

Use by local application twice a day for 4 weeks on the ichthyotic areas of the skin.

Of course, the invention includes all the constituent means technical equivalents of the means described, as well as the various combinations thereof. In particular, the invention covers not only the cosmetic or pharmaceutical treatment of the skin, but also that of the integuments such as the hair and nails.

What is claimed is:

1. A method for the treatment of the epidermis of patients suffering from the signs of aging, or otherwise suffering from dry skin, inflammation, solar erythema, skin allergies; or for the prevention of maladies associated with free radical formation, comprising topically administering an effective amount of at least one prunella component selected from among the group consisting of:

a) a prunella extract prepared by a solvent extraction of the prunella plant wherein said solvent is selected from among the group consisting of water, alcohols containing from 1 to 4 carbon atoms, chlorinated organic solvents containing 1 to 2 carbon atoms, organic esters containing from 3 to 6 carbon atoms, and mixtures thereof;

b) a prunella saponin obtained from said extract; and c) a mixture thereof.

2. The method of claim 1, wherein said extract of prunella plant is from the whole part thereof.

3. The method of claim 1, wherein said extract of said prunella plant is from the aerial parts thereof.

4. A method for topically treating the epidermis by a mechanism selected from the group consisting of (1) stimulating an increase in the number of keratinocytes; (2) inhibiting phospholipase A2; (3) anti-phlogistic activity; and (4) normalizing the differentiation of keratinocytes, said method comprising a topical application of an effective amount of all least one prunella component selected from among the group consisting of:

a) a prunella extract prepared by a solvent extraction of the prunella plant wherein said solvent is selected from among the group consisting of water, alcohols containing from 1 to 4 carbon atoms, chlorinated organic solvents containing 1 to 2 carbon atoms, organic esters containing from 3 to 6 carbon atoms, and mixtures thereof;

b) a prunella saponin obtained from said extract; and c) a mixture thereof.

5. The method of claim 4, wherein said prunella component is obtained by methanol extraction from *Prunella vulgaris* L.

6. The method of claim 1, wherein said prunella component is obtained by methanol extraction from *Prunella vulgaris* L.

7. The method of claim 1, wherein said prunella component is contained in a topically acceptable excipient.

8. The method of claim 1, wherein said prunella component is mixed with a pharmaceutically or cosmetically acceptable excipient, vehicle or carrier to provide a composition wherein the concentration of prunella component ranges between 0.001% and 5% by weight of the total composition.

9. The method of claim 1, wherein said prunella component is obtained from *Prunella vulgaris* L.

10. The method of claim 1, wherein the extract of prunella is obtained by carrying out a primary extraction with a solvent selected from the group consisting of water, alcohols, chlorinated solvents, organic esters, and a mixture of said solvents.

11. The method of claim 10, wherein said primary extraction is performed with a solvent selected from the group consisting of water, methanol, ethanol, a methanol/water mixture, an ethanol/water mixture, chloroform and dichloromethane.

12. The method of claim 10, wherein the treatment is performed with a mixture of prunella saponins.

13. The method of claim 10, wherein said method further comprises applying an effective amount of at least one other active substance selected from the group consisting of a xanthine, a vitamin, a vitamin ester, tyrosine, a tyrosine ester, quinine, a quinine ester, a rubefacient, a papilla fibroblast culture supernatant, a keratin hydrolyzate, a trace element, a bisbenzylisoquinoline alkaloid, a 5-α-reductase inhibitor, cyproterone acetate, 6-piperidino-2,4-diaminopyrimidine-3-oxide, azelaic acid, an azelaic acid ester, a 1,4-dimethyl-4-azasteroid and an extract of Serenoa repens.

14. The method of claim 13, wherein said vitamin is selected from the group consisting of vitamin. A, vitamin B and vitamin E.

15. The method of claim 13, wherein said tyrosine is selected from the group consisting of glucose tyrosinate and malyl tyrosine.

16. The method of claim 13, wherein said bisbenzylisoquinoline alkaloid is selected from the group consisting of oxyacanthine and cepharantine.

17. The method of claim 13, wherein said 1,4-dimethyl-4-azasteroid is 17-β-N,N-diethyl-carbamoyl-4-methyl-4-aza-5-a-androstan-3-one.

18. The method of claim 13, wherein said method further comprises applying said prunella component in combination with a lipidic component selected from the group consisting of hydrated lipidic lamellar phases and liposomes.

* * * * *

UNITED STATES PATENT AND TRADEMARK OFFICE
CERTIFICATE OF CORRECTION

PATENT NO. : 5,624,673
DATED : April 29, 1997
INVENTOR(S) : Frederic Bonte et al.

It is certified that error appears in the above-indentified patent and that said Letters Patent is hereby corrected as shown below:

ON THE TITLE PAGE:

Item [73], please change the Assignee's name from "LYMH Recherche" to --LVMH Recherche--; and After item [87], please insert --[30] Foreign Application Priority Data June 4, 1991 [FR]    France....................91/06757--

Signed and Sealed this

Second Day of September, 1997

Attest:

BRUCE LEHMAN

Attesting Officer

Commissioner of Patents and Trademarks